United States Patent
Hazard et al.

(10) Patent No.: US 9,421,387 B2
(45) Date of Patent: Aug. 23, 2016

(54) IMPLANTABLE BODY WITH A LEAD AND WITH AN ENGAGEMENT WING

(71) Applicant: Advanced Bionics AG, Staefa (CH)

(72) Inventors: Steven A. Hazard, Castaic, CA (US); Christine Marr, Castaic, CA (US)

(73) Assignee: ADVANCED BIONICS AG, Staefa (CH)

( * ) Notice: Subject to any disclaimer, the term of this patent is extended or adjusted under 35 U.S.C. 154(b) by 0 days.

(21) Appl. No.: 14/429,727

(22) PCT Filed: Sep. 20, 2012

(86) PCT No.: PCT/US2012/056420
§ 371 (c)(1),
(2) Date: Mar. 19, 2015

(87) PCT Pub. No.: WO2014/046662
PCT Pub. Date: Mar. 27, 2014

(65) Prior Publication Data
US 2015/0246234 A1 Sep. 3, 2015

(51) Int. Cl.
*A61N 1/375* (2006.01)
*A61N 1/05* (2006.01)
*A61N 1/36* (2006.01)

(52) U.S. Cl.
CPC .............. *A61N 1/375* (2013.01); *A61N 1/0541* (2013.01); *A61N 1/36032* (2013.01)

(58) Field of Classification Search
None
See application file for complete search history.

(56) References Cited

U.S. PATENT DOCUMENTS

| | | | |
|---|---|---|---|
| 6,309,410 | B1 | 10/2001 | Kuzma et al. |
| 6,889,094 | B1 | 5/2005 | Kuzma et al. |
| 8,235,886 | B2 | 8/2012 | Bernhard et al. |
| 8,489,195 | B2 | 7/2013 | Dalton et al. |
| 2006/0116743 | A1 | 6/2006 | Gibson et al. |
| 2008/0195178 | A1 | 8/2008 | Kuzma |
| 2008/0312717 | A1 | 12/2008 | Gantz |
| 2009/0099658 | A1 | 4/2009 | Dalton et al. |
| 2009/0216324 | A1 | 8/2009 | Leigh et al. |
| 2009/0254163 | A1 | 10/2009 | Gibson |
| 2010/0049318 | A1 | 2/2010 | Jolly et al. |
| 2011/0208303 | A1 | 8/2011 | Gibson |
| 2011/0245891 | A1 | 10/2011 | Fritsch et al. |
| 2016/0001076 | A1 | 1/2016 | Nielsen |

FOREIGN PATENT DOCUMENTS

| | | |
|---|---|---|
| EP | 1819303 B1 | 6/2012 |
| WO | 2007053882 | 5/2007 |
| WO | 2013054312 | 4/2013 |

OTHER PUBLICATIONS

Timothy B. Molony et al. "Device Fixation in Cochlear Implantation: Is Bone Anchoring Necessary" The Laryngoscope, vo. 120, Sep. 2010, pp. 1837-1839.
"Nucleus C1512 cochlear implant with Contour Advance electrode, Surgeon's Guide" Cochlear Ltd., Apr. 23, 2009, p. 1-32.

*Primary Examiner* — Brian T Gedeon
(74) *Attorney, Agent, or Firm* — Steven L. Nichols; Fabian VanCott (57) ABSTRACT

An implant system includes an implantable body (102), a lead (190) connected to the implantable body comprising at least one electrode, and engagement wings (400) mechanically joined to the implantable body to engage an undercut bone structure (405) to prevent motion of the implantable body toward the electrode after implantation.

16 Claims, 8 Drawing Sheets

```
Placing a shaped polymer sheet at an intersection
between a lead and a processor such that the
polymer sheet extends outward from either side of
the lead
705
```
↓
```
Overmolding the processor, lead and polymer
sheet to join the polymer sheet to the lead and
the processor to produce engagement wings
extending outward from either side of the lead
710
```

```
Create an undercut bone cavity
805
```
↓
```
Insert the engagement wings into the undercut
bone cavity
810
```

*Fig. 8*

IMPLANTABLE BODY WITH A LEAD AND WITH AN ENGAGEMENT WING

BACKGROUND

A variety of implantable devices can be used to augment or replace natural biological functions. For example, cochlear implants can be used to provide a sense of hearing to deaf or severely hard of hearing patients. Cochlear implants typically include an exterior portion and an implant portion. The implanted portion includes a processor, antenna, and electrode array that is implanted within or near the cochlea or auditory nerve. The electrode array is electrically driven by the implanted processor and antenna. The antenna receives external signals and electrical power. These signals and power are used by the processor selectively simulate the cochlea using the electrode array. The implanted processor and antenna are typically implanted under the patient's skin and connected to the electrode by a multi-wire lead.

Stabilizing implanted devices in the biological tissues can be challenging. Biological systems are typically dynamic with a wide range of forces that are exerted on the implant. For example, preventing the implanted processor and antenna in a cochlear implant from shifting after implantation can be important for a number of reasons. If the implanted processor and antenna shift after implantation, then wires in the lead can be damaged or the electrode array can be displaced. Additionally, shifting of the processor and antenna can cause tissue trauma and associated biological responses.

BRIEF DESCRIPTION OF THE DRAWINGS

The accompanying drawings illustrate various examples of the principles described herein and are a part of the specification. The illustrated examples are merely examples and do not limit the scope of the claims.

Throughout the drawings, identical reference numbers designate similar, but not necessarily identical, elements.

DETAILED DESCRIPTION

Cochlear implants currently rely on recessing the processor "can" or titanium portion into a drilled out bony recess on the skull to assist in stabilizing the processor and antenna. Surgeons are instructed to suture over the processor utilizing non-absorbable sutures. This requires surgeons to drill holes adjacent to the bony recess in an effort to create a small diameter tunnel (between two holes) to use as tie-down anchor points. Some surgeons drill an angled tie-down hole that enters the side wall of the bony recess. Other approaches use a screw fixation system using eyelets on the implant package to stabilize it on the underlying bone. Alternatively, titanium screws can be used as anchors for sutures or mesh.

Within the industry, many surgeons have moved away from these traditional approaches and have adopted a "pocket" approach. The pocket approach includes creating a "pocket" between the skull and the periosteum and relies heavily on the attachment of periosteum to the skull around the edges of the pocket to minimize motion of the implanted body. In this approach, no drilling is performed to create a bony recessed bed and no tie-downs or screws are used. In some cases surgeons are not drilling a protective channel for the electrode lead as it exits from the mastoid cavity. This approach requires careful attention to minimize the size of the pocket. However, the pocket is open on the anterior/inferior direction to allow access to the site for implant placement. This is also the direction in which implant migration is most likely to occur.

The reasons for an increase in the number of surgeons relying on the "pocket" approach vary. In the very young implanted population, the skull thickness is minimal and the surgeons might expose dura during any drilled bony recessed bed effort. Consequently, many surgeons are avoiding any bony recessed beds in the youngest of implanted patients. Other reasons for not drilling the bony recessed bed include increased time in surgery, questions regarding the necessity, and concerns over damage to the dura (cerebrospinal fluid (CSF) leaks, subdural bleeding).

Consequently, there is a need for an implant stabilization system that does not require formation of a bone bed and is compatible with the "pocket" approach that is gaining favor with surgeons. This implant stabilization system would ideally prevent the implanted body from migrating out of the periosteal pocket in the previously mentioned anterior/inferior direction.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with the example is included in at least that one example, but not necessarily in other examples.

Figure 1:
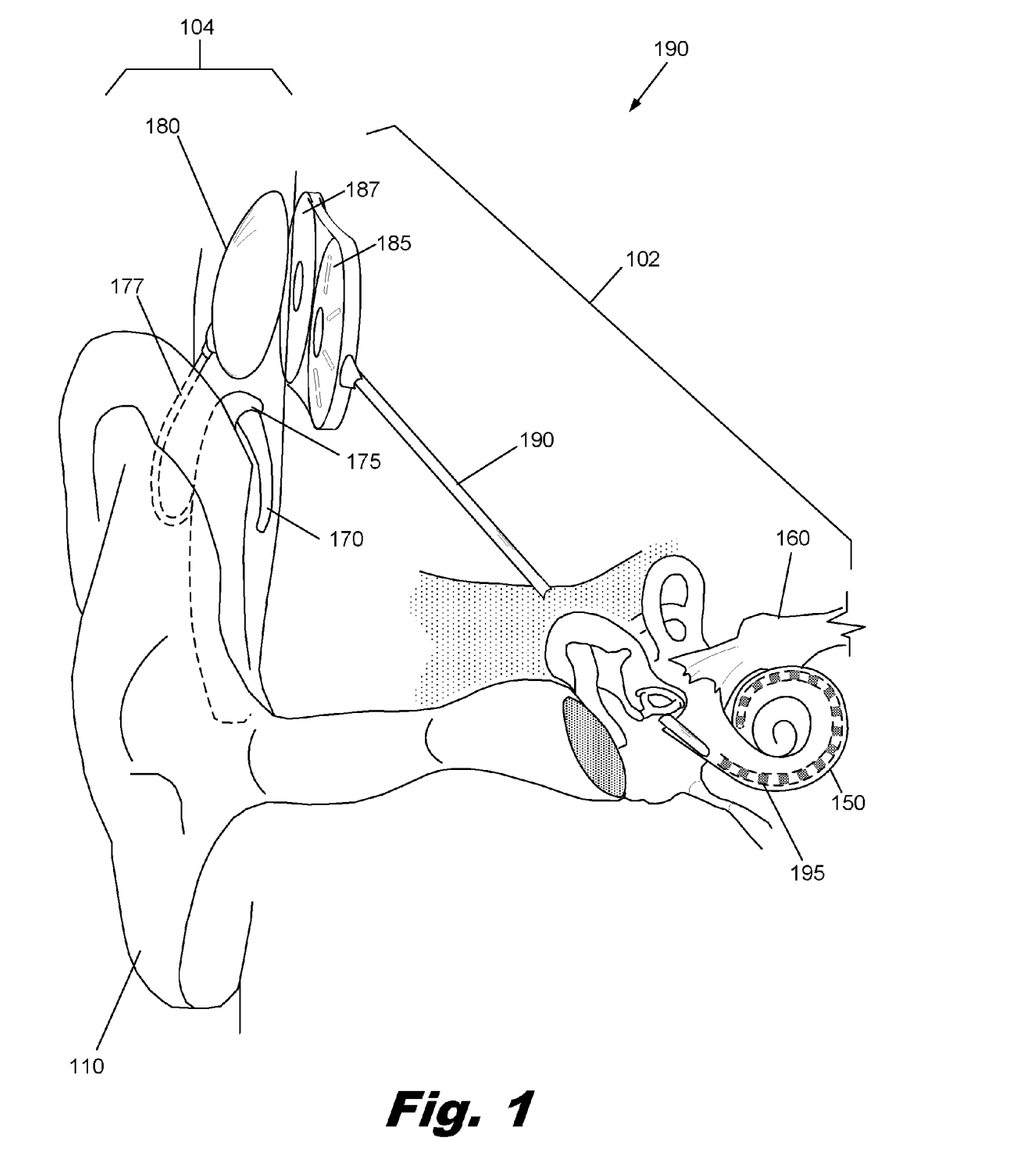
FIG. 1 is a diagram showing one illustrative example of a cochlear implant system that is surgically placed within a patient, according to one example of principles described herein.
Figure 2:
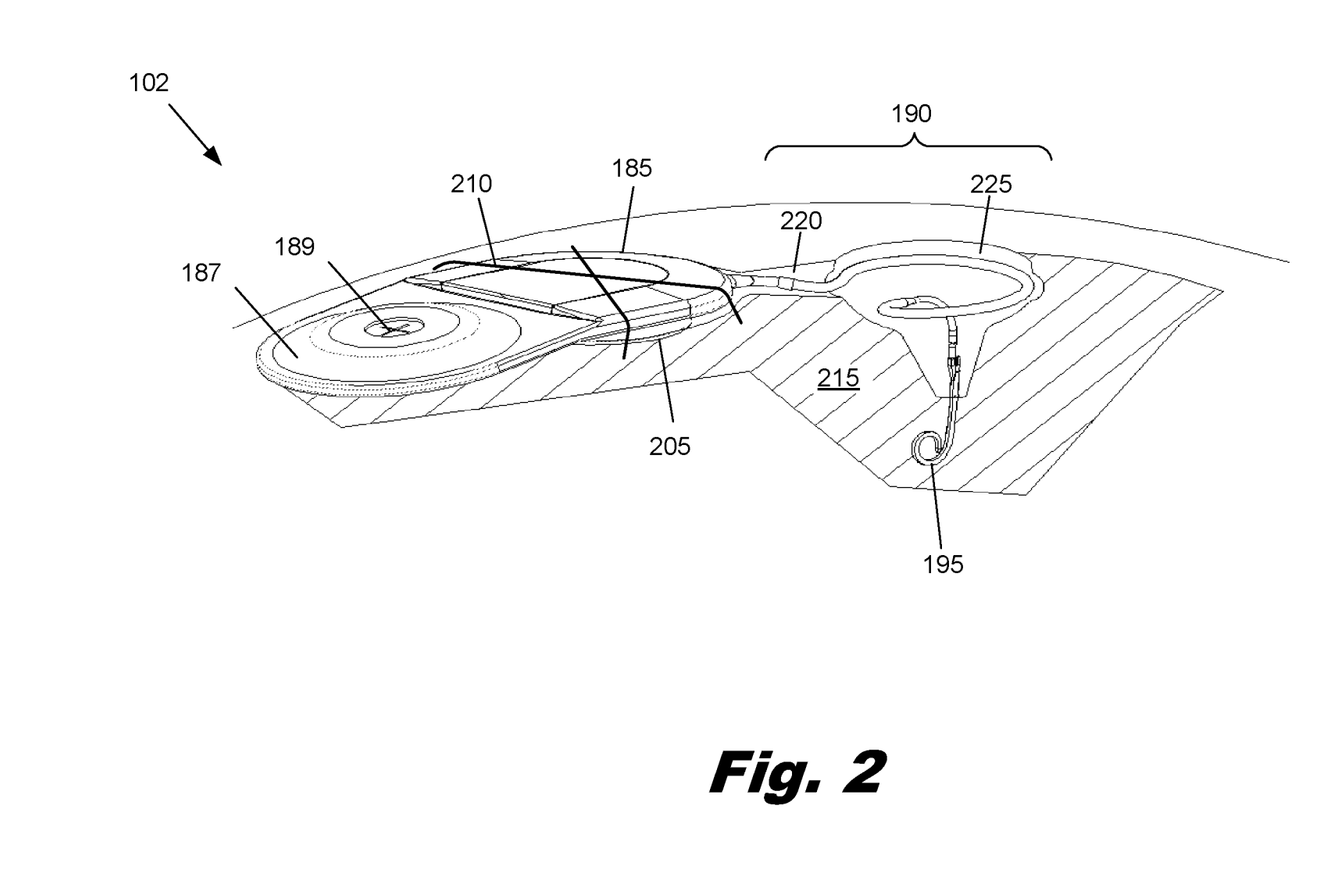
FIG. 2 is a partially cut away perspective view of internal components of a cochlear implant placed in surgically formed cavities and secured using sutures, according to one example of principles described herein.
Figure 3A:
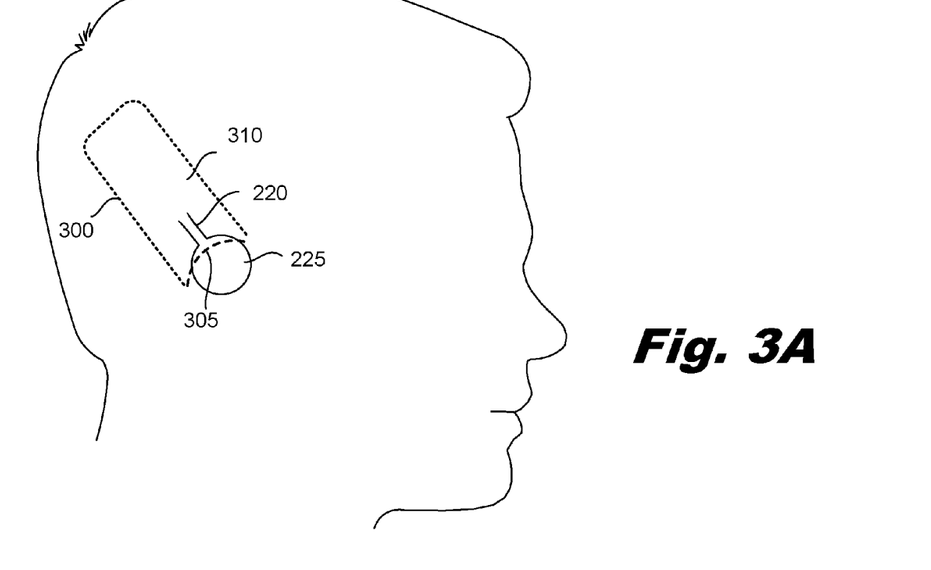
FIG. 3A is a side view of a patient's head showing surgically formed features during an implantation procedure, according to one example of principles described herein.
Figure 3B:
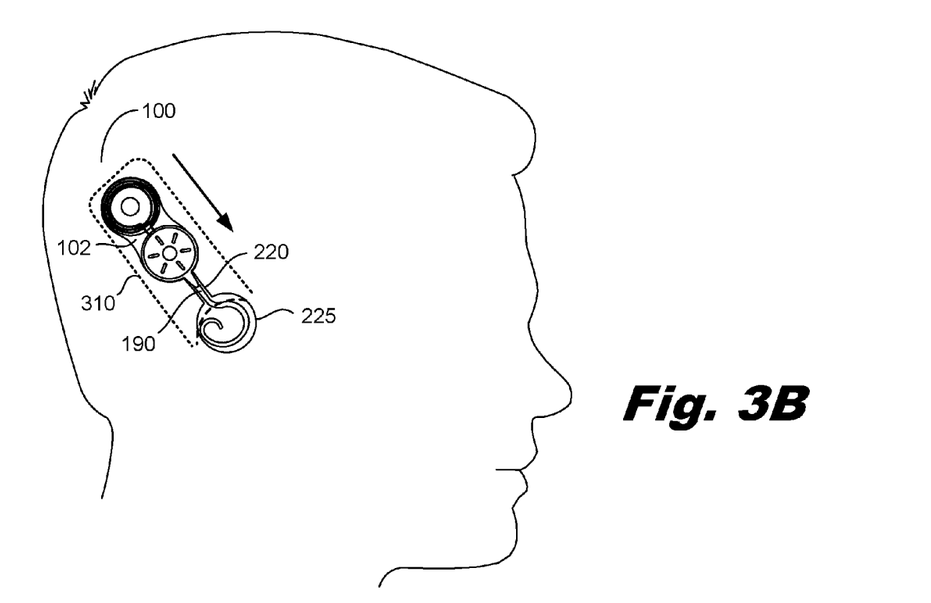
FIG. 3B shows a surgically placed internal portion of the cochlear implant, according to one example of principles described herein.

FIG. 1 gives a general overview of an illustrative cochlear implant system. FIG. 2 shows a bone bed approach for retaining an internal portion of the cochlear implant, FIGS. 3A-3B show the periosteal pocket approach. FIGS. 4A-4D describe illustrative engagement wings that can be used to stabilize the internal portion of a cochlear implant or other implanted device. The approaches described in FIGS. 4A-4D may be particularly suitable for use in conjunction with the periosteal pocket implantation approach.

FIG. 1 is a diagram showing one illustrative example of a cochlear implant system (100) that includes an internal implanted portion (102) and an external portion (104). The cochlear implant system (100) provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

The internal implanted portion (102) of the cochlear implant includes an electrode array (195) that is surgically placed within the patient's cochlea. Unlike hearing aids, the cochlear implant (202) does not amplify sound, but works by directly stimulating any functioning auditory nerve cells inside the cochlea (150) with electrical impulses representing the ambient acoustic sound. This bypasses the defective cochlear hair cells that normally transduce acoustic energy into electrical energy.

The external portion (104) of the cochlear implant system (100) can include a Behind-The-Ear (BTE) unit (175), which contains the sound processor and has a microphone (170), a cable (177), and a transmitter (180), The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna assembly (187) by electromagnetic transmission, In some cochlear implant systems, the transmitter (180) is held in place by magnetic interaction with a magnet (189) in the underlying antenna assembly (187).

The internal portion (102) of the cochlear implant system (100) includes an internal processor (185), an antenna assembly (187), and a cochlear lead (190) having an electrode array (195). The internal processor (185) and antenna assembly (187) are secured beneath the user's skin, typically above and behind the pinna (110). The antenna assembly (187) receives signals and power from the transmitter (180). The internal processor (185) receives these signals and operates on the signals to generate modified signals. These modified signals are then sent through the cochlear lead (190) to the electrode array (195), which is at the distal portion of the cochlear lead (190) and is implanted within the cochlea (150). The electrode array uses the modified signals and provides electrical stimulation to the auditory nerve (160).

FIG. 2 is a diagram of the internal portion (102) surgically implanted into a patient, The antenna (187), internal processor (185), and encapsulation make up an "implantable body" (185, 187) and are positioned beneath the skin of the patient. In some examples, a mastoidectomy is performed to create a mastoid cavity (225). The mastoid cavity exposes the cochlea and allows the electrode array (195) to be inserted through a cochleostomy into the cochlea.

Portions of the bone (215) underlying the processor (185) can be removed to create a recessed bone bed (205) to reduce the profile of the processor. The cochlear lead (190) passes through a lead channel (220) in the bone (215) that connects the mastoid cavity (225) and the bone bed (205). The processor can be held into the bone bed (205) using non-absorbable sutures (210). The combination of the sutures (210) and bone bed (205) hold the implantable body (185, 187) in place. This prevents damage to the device and prevents irritation of the surrounding tissues. However, creating the bone bed (205) and attachment points for sutures can be time consuming and increase the likelihood of a surgical tool or drill accessing the underlying dura, particularly in younger patients that have thin skulls. In some very rare cases dura tears or cuts have been experienced by surgeons causing a CSF leak requiring repair.

FIGS. 3A and 3B describe the "pocket" approach that does not use a bone bed or sutures to stabilize the implanted body. FIG. 3A is a side view of a patient's head showing surgically formed features during an implantation procedure. The surgeon makes an incision (305) through the skin and periosteum. This incision is typically an arc about three cm long behind the external ear. The surgeon forms a mastoid cavity (225) and lead channel (220) by removing bone from the patient skull. The thickness of the skull is typically thicker near the mastoid and gradually decreases in thickness away from the mastoid. The surgeon also forms a pocket (310) between the periosteum and the skull by separating the periosteum from the underlying bone. The outline (300) of the pocket is shown as a dashed line. The periosteum is a tough protective membrane that covers and supplies nutrients to bones. The periosteum includes two layers: a tough outer layer of dense connective tissue and an inner osteogenic layer. The periosteum is attached to bone by strong collagenous fibers ("Sharpey's fibers"). Because of the toughness of the periosteum and relatively strong attachment of the periosteum to the bone, the pocket can be fairly effective in retaining the implanted body on the three sides of the pocket.

FIG. 3B shows the internal portion (102) of a cochlear implant system (100) inserted into the pocket (310), with a portion of the cochlear lead (190) in the lead channel (220) and the remainder of the lead coiled in the mastoidectomy cavity (225). As discussed above, the electrode array on the end of the lead passes through mastoidectomy, through a cochleostomy and into the cochlea. In this example, the surgeon has not formed a bone bed to receive the underside of the processor can or created sutures to hold the cochlear implant in place. Thus, there are minimal mechanical restraints that prevent the cochlear implant from migrating downward out of the pocket and toward the mastoidectomy as shown by the arrow point downward and to the right.

Several different forces can tend to encourage this migration out of the periosteal pocket. When the patient is erect, gravity tends to pull the cochlear implant downward. Additionally, the tough periosteum that is stretched over the cochlear implant exerts compression forces that tend to encourage migration of the implant out of the pocket. Other forces that may rend to cause migration include impact forces, manipulation of the scalp and adjacent bones, or other forces.

In a small number of cases, these forces can result in migration of the implanted body out of the periosteal pocket. This can have a number of negative impacts, including damage to the cochlear implant, negative biological reactions, and patient discomfort. For example, motion of the processor toward the mastoidectomy can result in kinking or breakage of the wires in the lead (190).

Figures 4A, 4B:
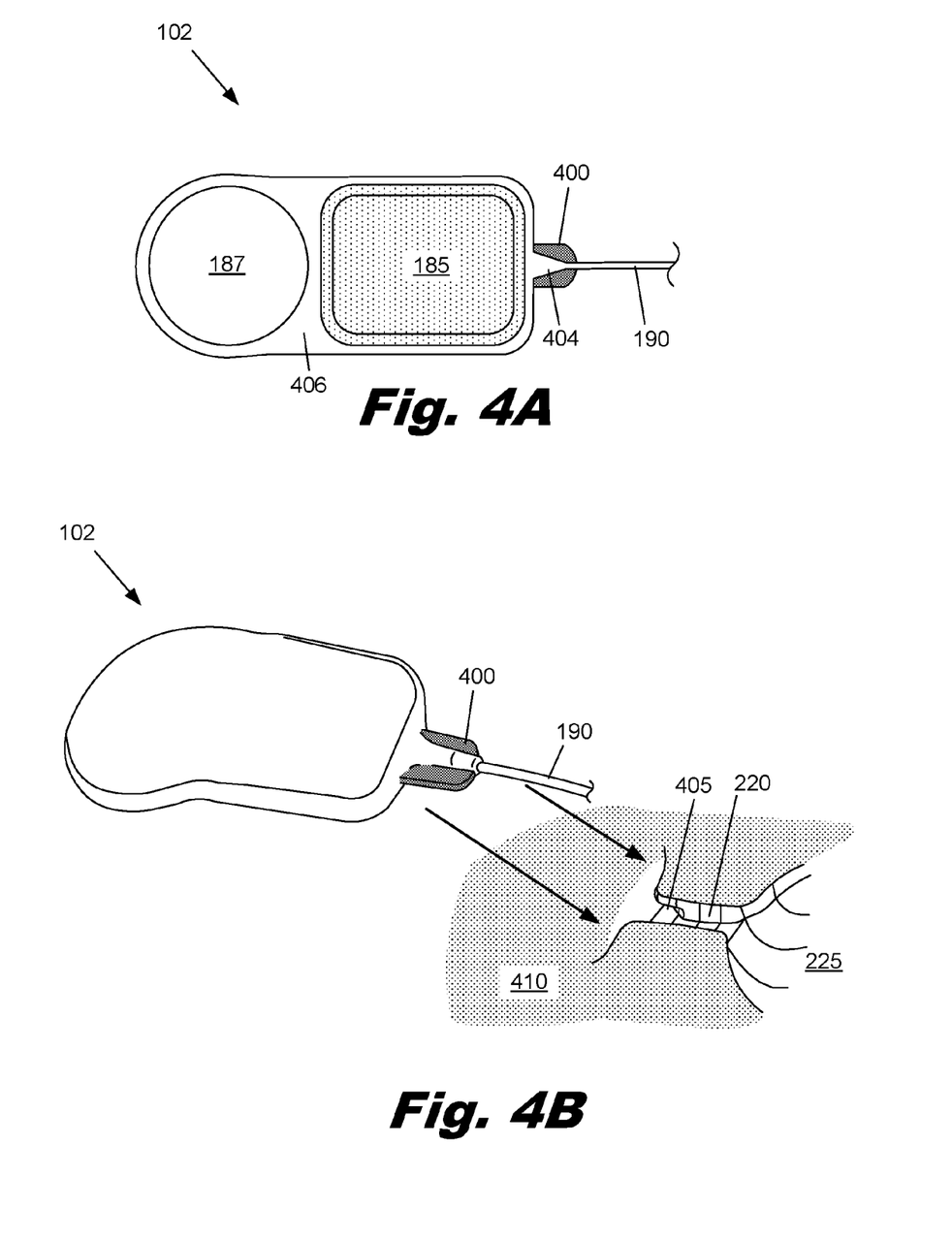
FIG. 4A is a top view of an internal portion of a cochlear implant with wings at the exit of the electrode lead from the implantable body, according to one example of principles described herein.
FIG. 4B is a perspective view of an implantable body with engagement wings being positioned in an undercut portion of a lead channel, according to one example of principles described herein.

FIGS. 4A-4D show an illustrative cochlear implant with engagement wings that prevent motion of the processor and antenna toward the mastoidectomy. FIG. 4A is a top view of an internal portion (102) of cochlear implant with engagement wings (400) at the exit of the lead (190) from the processor (185). In this example, wings extend laterally from either side of the lead (190) and have a rounded front profile and parallel sides. The wings (400) are wider than the strain relief fantail (404) that connects the lead to the implantable body (185, 187).

FIG. 4B shows a perspective view of a cochlear implant with engagement wings being positioned in an undercut portion of a lead channel. As shown in FIGS. 3A, a mastoidectomy cavity (225) and a lead channel (220) are formed. To provide engagement for the wings, undercut features (405) are created at the end of the lead channel opposite the mastoidectomy cavity (225). These undercut features (405) are formed on either side of the channel and are adapted to receive the engagement wings (400). For example, the undercut features (405) may be formed by undercutting the sides of the lead channel (220) by 1-2 millimeters along a 1 centimeter length of the channel. FIG. 4B shows the location of the cochlear implant when the engagement wings are inserted into the undercut features. In practice, the cochlear implant may be slid into the periosteal pocket through the surgical incision until the wings slide over and past the undercut features. The motion of the cochlear implant is then reversed and the engagement wings are guided downward and into the undercut features. The tension in the periosteal pocket and gravity forces tend to hold the wings in place in the undercut features. The lead channel (220) is formed in the bone (410).

Figure 4C:
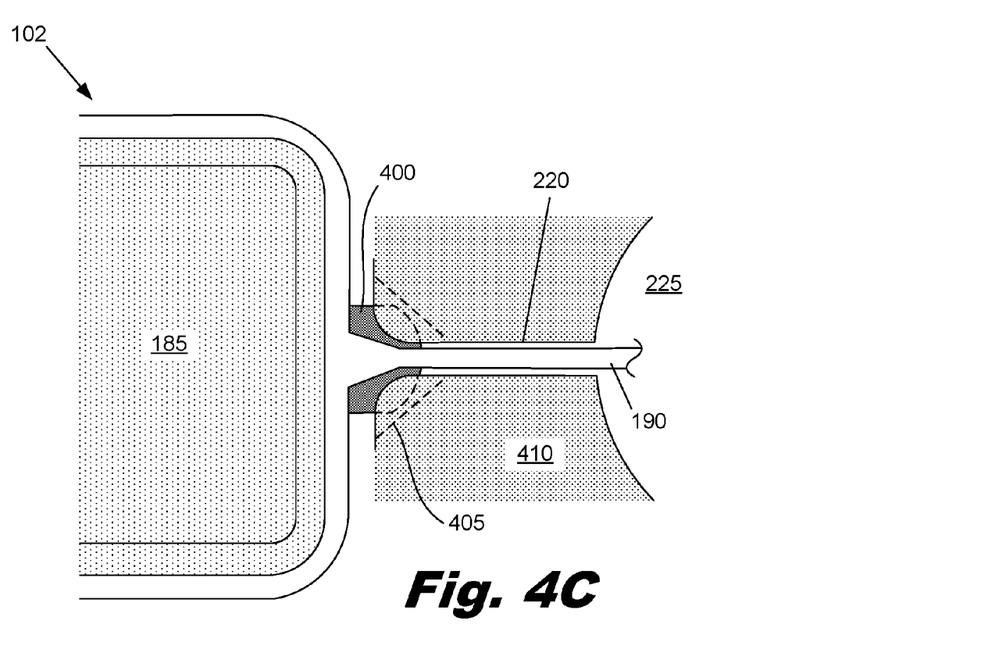
FIG. 4C is a top view of an implantable body with engagement wings placed in an undercut portion of a lead channel, according to one example of principles described herein.

FIG. 4C is a partial top view of an internal portion (102) of a cochlear implant with engagement wings (400) placed in the undercut features (405) of a lead channel (220). In this figure, dashed lines are used to show lines that are hidden in the undercut features (405). Diagonal dashed lines show the extent of the undercut. In this example the undercut has a triangular shape. The lead channel (220) is formed in the bone (410).

Figure 4D:
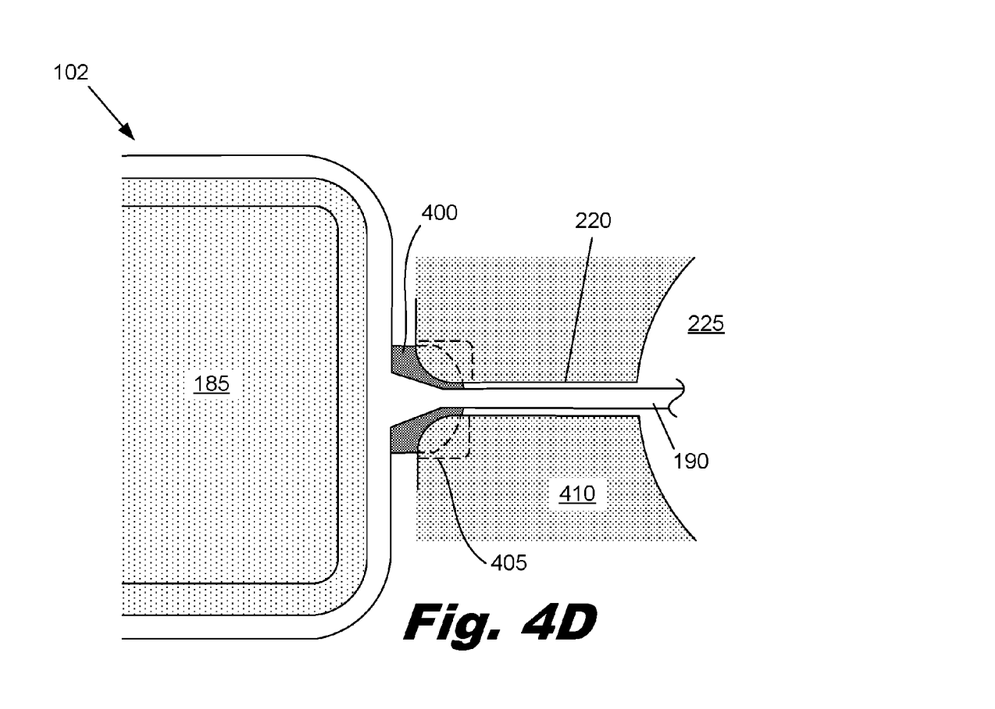
FIG. 4D is a top view of an implantable body with engagement wings placed in an undercut portion of a lead channel, according to one example of principles described herein.

FIG. 4D shows a top view of an internal portion (102) of a cochlear implant system (100) with engagement wings (400) placed in rectangular undercut features (405). As discussed above, when the engagement wings (400) are placed in the undercut features (405), the forward motion of the processor (185) is arrested as the wings engage with the undercut features. This prevents undesirable kinking of the lead (190) and retains the lead in the lead channel (220). The lead channel (220) is formed in the bone (410).

Figure 5A:
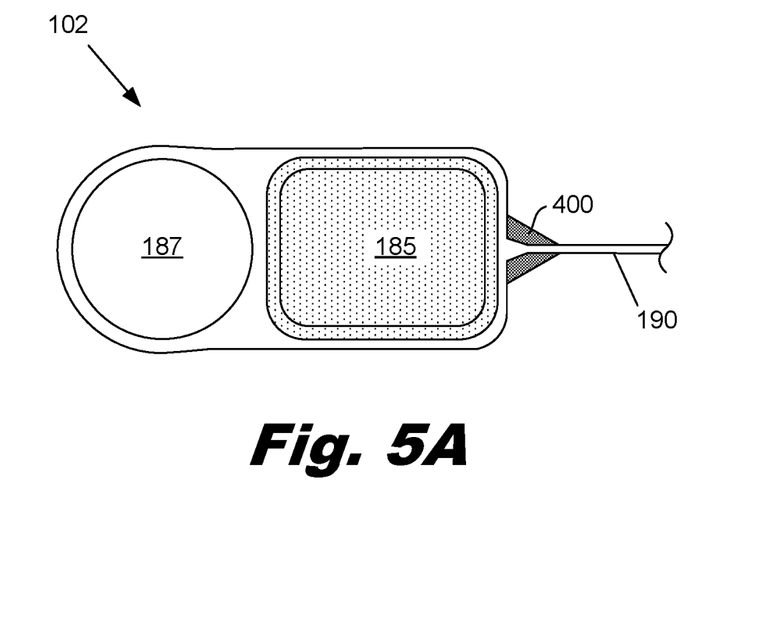
FIG. 5A is a top view of an implantable body with wings at the exit of the electrode lead from the implant, according to one example of principles described herein.
Figure 5B:
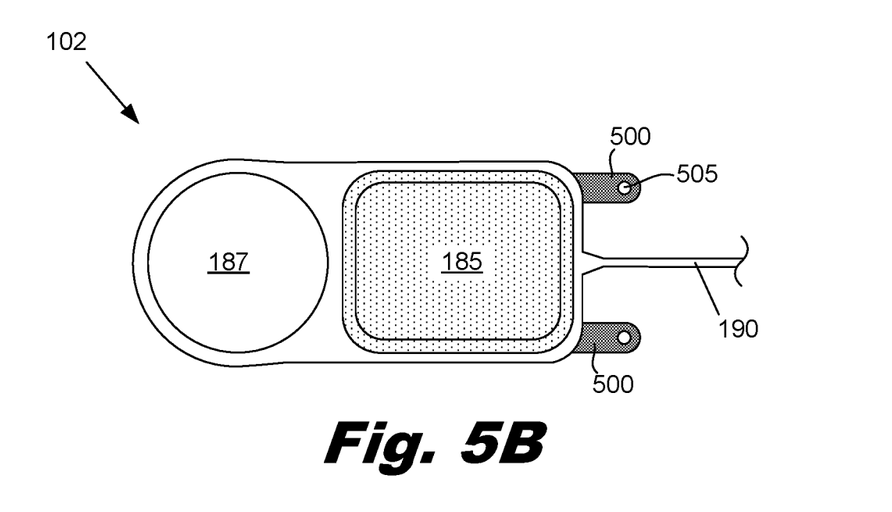
FIG. 5B is a top view of an implantable body with two laterally separated wings, according to one example of principles described herein.

FIGS. 5A and 5B illustrate several alternative examples of engagement wings. FIG. 5A is a top view of an internal portion (102) of a cochlear implant with triangular engagement wings (400) at the intersection of the lead from the implant body (185, 187). Triangular engagement wings (400) may have a number of advantages, including the ability to engage with undercut features having a variety of widths.

FIG. 5B is a top view of a cochlear implant with two laterally separated engagement wings (500). These laterally separated wings (500) may or may not engage undercut bone features. In some examples, at least one of the laterally separated wings (500) may include a hole (505) that can be used to fasten the wing to underlying or overlying tissue with a fastener such as suture or a screw. This will hold the internal portion (102) of the cochlear implant system (100) in place. The wings stabilize the implantable body so it cannot rotate or shift toward the electrode (anteriorly/inferiorly).

This approach can reduce the risk of lead breakage because it does not use the lead for stabilization of the implantable body. The engagement wings also provide the surgeon with flexibility to perform the surgery in a manner with which that surgeon is most comfortable and is suited to the needs of the patient. For example, the wings could be used with or without creating a bone bed. Further, the surgeon could select sutures or screws to secure the implantable body. The surgeon could ignore the wings and recess the implant in a ramped or complete bone bed. If the engagement wings are not used, there is no need to remove them.

Figure 6A:
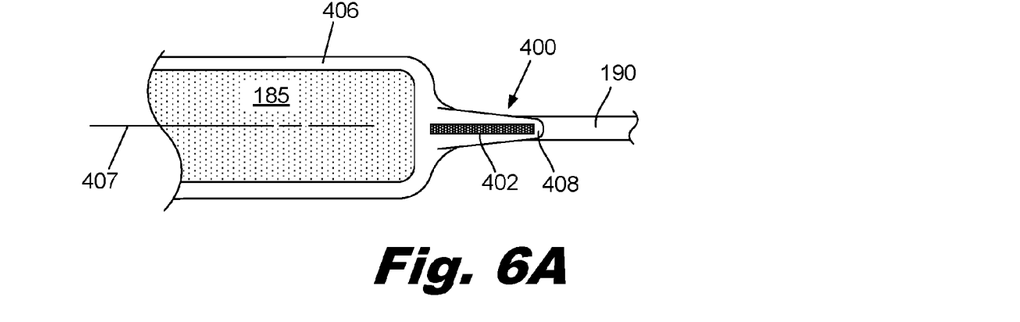
FIGS. 6A-6D show various examples of engagement wings, according to one example of principles described herein.

FIGS. 6A-6D are cross sectional diagrams of various positions and designs for engagement wings (400). FIG. 6A shows an engagement wing (400) that has a central structural core (402) and a tapered silicone overmold which forms a strain relief fantail (404). The engagement wing (400) is aligned with both the lead (190) and the centerline of the processor (407). The tapered shape of the wing (400) can provide a number of advantages including secure engagement of undercut features having cavities of various sizes. This can reduce the precision needed to form the undercut features.

Figure 6B:
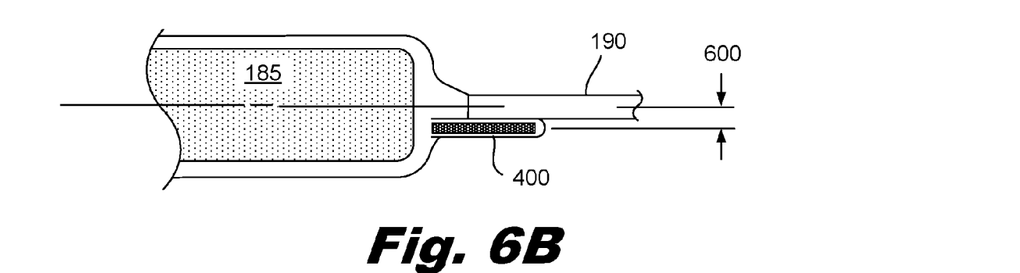

FIG. 6B shows an engagement wing (400) that has an offset (600) from the lead (190) and center line of the processor (185). The offset (600) can be either above or below the centerline of the processor and/or lead. The offset can provide a number of advantages including freedom to create the undercut features at any suitable level of the skull. For example, the offset of the wing from the lead/processor centerline allows for lead channel with a minimal depth, while the undercut features are deeper to ensure the desired thickness of bone over the undercut cavity.

Figure 6C:
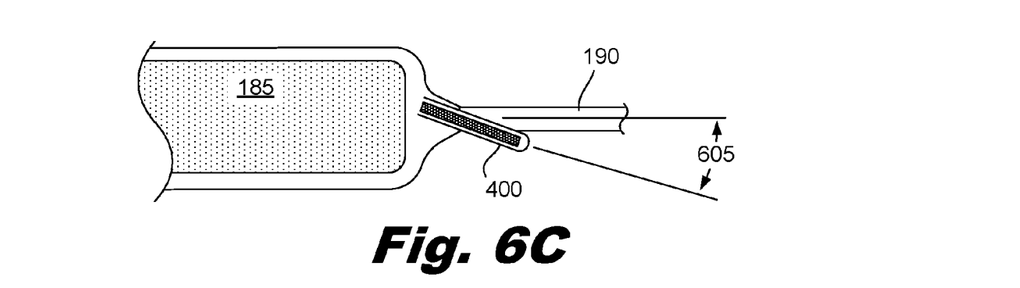

FIG. 6C shows an angled engagement wing (400) that has been formed at an angle. (605) with respect to the lead (190) and/or processor (185) centerline. This configuration can be used with undercut features that have been formed at an angle. Forming undercut features at an angle may be more convenient for a surgeon to cut and may be especially suitable for patients with thicker skulls.

Figure 6D:
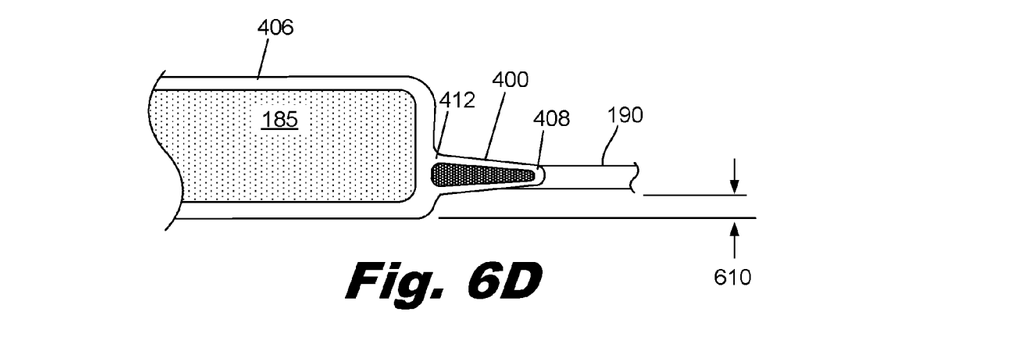

FIG. 6D shows an engagement wing (400) that is inline with the lead (190) but has an offset (610) from the bottom of the processor (185). As discussed and illustrated above, the lead (190) electrically and mechanically connects the implanted processor to the electrode array. Silicone overmolding covers the implanted processor and lead and forms a strain relief fantail (404) extending from the processor over a proximal portion of the lead. A lead channel is formed in the patient's bone and an undercut bone cavity is formed by widening a bottom portion of the lead channel adjacent to the processor. The widened bottom portion of the lead channel may be two to four millimeters greater than the upper portion of the lead channel and extends 6-14 millimeters down the length of the lead channel.

The engagement wings (400) are mechanically joined to the processor (185) and extend outward on either side of the lead (190) to engage the undercut bone cavity in order to prevent the motion of the processor (185) toward the electrode array after implantation. In this example, the engagement wings have a polyethylene terephthalate structural core and a compliant silicone overmold. The engagement wings include a rounded front radius with parallel sides as shown in FIGS. 4A-4D. The engagement wings also have a thinner distal edge (408) with increasing thickness to match a width of the strain relief fantail at the trailing edge (412) where the engagement wings join the processor. In some implementations, the wings are offset (610) approximately 1 millimeter above the bottom of the implant to allow the cochlear implant to be fitted into a bone bed if desired. FIG. 6D shows an example of a structural core that does not have a uniform thickness. In contrast, the structural core has a taper that matches the taper of the overall wing. This can result in a much stiffer wing configuration.

The designs shown in the figures above are only illustrative. The wings may be made from a variety of material. For example, the wings may be made from biocompatible polymer, composite, metals, or combinations thereof. For example, the wings may include structural core with silicone overmolding. In one example, the structural core is formed from structural polymers such as polyethylene terephthalate (PET), polytetrafluoroethylene (PTFE), polyether ether ketone (PEEK), poly(methyl methacrylate) (PMMA), polyethylene, or other suitable biocompatible polymer. In some examples, the wing overmold can be formed at the same time and using the same process as the processor overmold (406). For example, insert liquid injection molding can be used.

A variety of different types of wings and wing configurations could be used. For example, the wing may be an integral part of the titanium processor housing or it may be separated to allow greater flexibility. These wings may be tapered at the distal end (toward the electrode array) and increase in thickness as they join the implantable body (185, 187). In one implementation, the wings have a thin leading edge and a thicker trailing edge that matches the thickness of the strain relief fantail. Alternatively, the wings may have other shapes to engage with the undercut. The configurations of wings shown above are only examples. A number alternative configurations could be used. For example, the bottom of the wings and lead may be flush with the bottom of implant package overmolding. This configuration may be particularly well suited for patients with thinner bone structures and for implant designs that do not anticipate the surgeon will want to create a bone bed to recess the processor into the skull.

Figure 7:
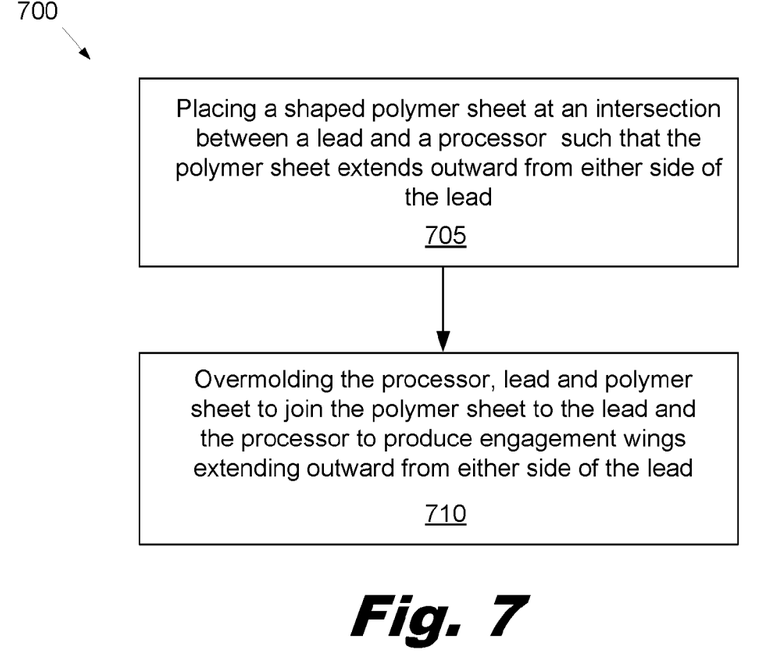
FIG. 7 is a flowchart of an illustrative method for forming an implantable body with engagement wings, according to one example of principles described herein.

FIG. 7 is a flowchart of a method for forming a cochlear implant with engagement wings. The method includes placing a polymer sheet at an intersection between a lead and a processor such that the polymer sheet extends outward from either side of the lead (block 705). The sheet can be formed in a variety of ways including using laser machining, molding, cutting, stamping or other techniques. The sheet may have a uniform thickness or a varying thickness.

The processor, lead, and polymer sheet are overmolded with a flexible polymer to join the polymer sheet to the lead and processor (block 710). This produces engagement wings extending outward from either side of the lead. The overmolding process may be accomplished in a number of different ways, including liquid insert molding. The flexible polymer may be medical grade silicone.

Figure 8:
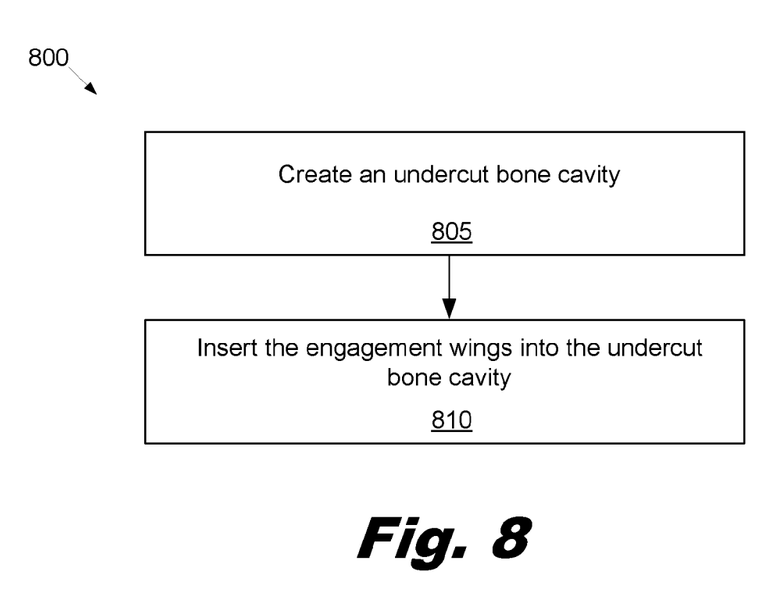
FIG. 8 is a flowchart of an illustrative method for stabilizing a cochlear implant, according to one example of principles described herein.

FIG. 8 is a flowchart of a process for implanting a cochlear implant with engagement wings. As discussed above, various techniques can be used to form various cavities/pockets in the patient's tissues. This can include creating an undercut bone cavity (block 805). In the examples described above, the undercut bone cavity is shown as a widening of a bottom portion of a lead channel. However, the undercut bone cavity could be separate from the lead channel or associated with another cavity or structure. In some examples, such cochlear implants with flat ribbon leads connecting the processor to the electrode array, the lead channel may be omitted and the undercut bone cavity may be formed alone. Silicone rubber mockups that incorporate engagement wings and/or custom surgical instruments can allow for precise positioning and verification of the undercut bone cavity formed during surgery.

The engagement wings are inserted into the undercut bone cavity during positioning of the cochlear implant in the implant site (block 810). As discussed above, the engagement wings prevent the forward motion of the cochlear implant.

Although the description above uses a cochlear implant as an illustrative example of an implant that could be secured using engagement wings, the principles described above can be used for a variety of implanted devices. Engagement wings could be used to secure any implanted device, or portions of an implanted device, that are implanted over a suitable bony structure. For example, retinal implants and brain stimulators may all include a processor that is implanted over the skull.

In sum, the lead exit from the processor can be modified to form a set of thin engagement wings. The engagement wings are significant in that the cochlear implant has built in retention features. Building the retention features as a part of the device reduces the part count and makes implantation more straightforward. The engagement wings stabilize the "front" end of the implant and prevent migration of the implant toward the mastoidectomy, The engagement wings ensure that the exiting electrode lead is held down in the channel, providing protection as well as retention. Keeping the electrode lead from slipping out of the channel protects it from damage between the skull and soft tissue. Further, the surgeon could ignore the wings and recess the implant in a ramped or complete bone bed. The wings stabilize the implantable body so it cannot rotate or shift forward toward the electrode (anteriorly). If the engagement wings are not used, there is no need for them to be removed.

A greater number of surgeons may choose to utilize this relatively simple and fast to install retention technique. The location of the undercut features is also beneficial. The bone is generally thicker closer to the mastoid cavity drilled by the surgeons for all age groups. The engagement wing retention technique can also be used with other devices, such as middle ear implants, deep brain stimulation devices, and other devices that are mounted to bony structures.

This stabilization technique is significantly less invasive than creating a bone bed. However, the surgeon can chose to use a recessed bone bed or a pocket technique with minimal differences in technique. The cochlear implants with engagement wings can be designed so that the surgeon has a number of options for implantation. These options include: creating a full depth recessed bed per the current surgeons guide; create a shallower recessed bed; or creating only a periosteal "pocket". When a bone bed is formed, the wings may or may not be used. The surgeon may simply choose to ignore the wings and not create the undercut features. No modification of the device is needed if the surgeon chooses not to utilize the wings. Alternatively, the surgeon may create the undercut features and use the engagement wings in addition to the bone bead. When the surgeon chooses not to create a bone bed and relies on the engagement wings to prevent migration of the implant, the surgery may be performed more quickly, with less drilling of bone. This decreases risks for the patient and has a lower chance of exposing the dura mater underlying the bone. The engagement wing also provides greater stability than a purely pocket approach during magnetic resonance imaging (MRI).

The preceding description has been presented only to illustrate and describe examples of the principles described. This description is not intended to be exhaustive or to limit these principles to any precise form disclosed. Many modifications and variations are possible in light of the above teaching.

What is claimed is:

1. An implant system comprising:
    an implant body;
    a lead connected to the implant body comprising at least one electrode; and
    an engagement wing mechanically joined to the implant body and mechanically joined to the lead to engage an undercut bone structure to resist motion of the implantable body toward the electrode after implantation.

2. The system of claim 1, wherein the wing comprise two wings connected to either side of the lead.

3. The system of claim 1, wherein the wing comprises a structural core overmolded with a compliant polymer.

4. The system of claim 3, wherein the structural core comprises polyethylene terephthalate and the compliant overmold comprises silicone.

5. The system of claim 3, wherein the structural core comprises a biocompatible metal.

6. The system of claim 1, further comprising a strain relief fantail extending from the implantable body over a proximal portion of the lead, wherein the wing comprises a thinner distal edge and increasing in thickness to match a width of the strain relief fantail.

7. The system of claim 1, wherein the wing is offset from the midline of the lead.

8. The system of claim 1, wherein the wing comprises a rounded front radius with parallel sides.

9. The system of claim 1, wherein the wing is offset from a bottom of the implantable body by approximately one millimeter to allow the implantable body to be recessed into a bone bed.

10. The system of claim 1, further comprising a lead channel to receive a portion of the lead, wherein the undercut bone structures comprise a widened portion of a lead channel.

11. The system of claim 1, further comprising two separate wings laterally offset from the lead, wherein at least one of the wings has a hole formed therein to receive a fastener.

12. A cochlear implant system comprising:
    an implanted processor including a processor can;
    an electrode array;
    a lead electrically and mechanically connecting the processor can to the electrode array;
    a silicone overmold covering the processor can and comprising a strain relief fantail extending from the processor can over a proximal portion of the lead;
    a lead channel formed in bone;
    an undercut bone cavity comprising a widened bottom portion of the lead channel adjacent to the processor can, in which the widened bottom portion of the lead channel has a width of approximately two to four millimeters greater than upper portion of the lead channel and extends approximately 6-14 millimeters down the length of the lead channel; and engagement wings mechanically joined to the processor and extending from either side of the lead to engage the undercut bone cavity to prevent motion of processor can toward the electrode array after implantation, wherein the engagement wings comprise a polyethylene terephthalate structural core and a compliant silicone overmold, and wherein the engagement wings comprise a rounded front radius with parallel sides and a thinner distal edge with increasing thickness to match a width of the strain relief fantail where the engagement wings join the processor can, wherein the wings are offset from a bottom of the processor can by approximately one millimeter to allow the processor can to be recessed into a bone bed.

13. A method for implant stabilization comprising:
    creating an undercut bone cavity; and
    inserting engagement wings connected to an implantable body into the undercut bone cavity.

14. The method of claim 13, further comprising:
    creating a three sided pocket between a periosteum and a bone layer; and
    inserting a cochlear implant with engagement wings into the three sided pocket prior to inserting the engagement wings into the undercut bone cavity.

15. The method of claim 14, in which distance from an entrance of undercut bone cavity to a back wall of the three sided pocket is less than the distance between a leading edge of the engagement wings and a most distal edge of a cochlear implant antenna, the method further comprising:
    inserting the cochlear implant to a back of the three sided pocket such that the most distal edge of the cochlear implant antenna contacts the back of the three sided pocket; and
    bending the cochlear implant to shorten the distance between the leading edge of the engagement wings and the most distal edge so that the engagement wings can be inserted into the entrance of undercut bone cavity.

16. A method for forming a cochlear implant with engagement wings, comprising:
    placing a polymer sheet at an intersection between a lead and a processor such that the polymer sheet extends outward from either side of the lead; and
    overmolding the processor, lead, and polymer sheet to join the polymer sheet to the lead and processor to produce engagement wings extending from either side of the lead.

* * * * *